(12) United States Patent
Henderson et al.

(10) Patent No.: US 6,897,015 B2
(45) Date of Patent: May 24, 2005

(54) DEVICE AND METHOD OF USE FOR DETECTION AND CHARACTERIZATION OF PATHOGENS AND BIOLOGICAL MATERIALS

(75) Inventors: Eric R. Henderson, Ames, IA (US); Saju R. Nettikadan, Ames, IA (US); Curtis L. Mosher, Ames, IA (US)

(73) Assignee: BioForce Nanosciences, Inc., Ames, IA (US)

( * ) Notice: Subject to any disclaimer, the term of this patent is extended or adjusted under 35 U.S.C. 154(b) by 455 days.

(21) Appl. No.: 10/160,372

(22) Filed: May 30, 2002

(65) Prior Publication Data

US 2002/0172943 A1 Nov. 21, 2002

Related U.S. Application Data

(63) Continuation-in-part of application No. 09/519,271, filed on Mar. 7, 2000, now Pat. No. 6,716,578, and a continuation-in-part of application No. 09/574,519, filed on May 18, 2000, now Pat. No. 6,573,369.

(51) Int. Cl.$^7$ ............................ C12Q 1/70; G02B 26/10
(52) U.S. Cl. ............................ 435/5; 435/7.1; 435/40.5; 359/196
(58) Field of Search ............................ 435/5, 7.1, 40.5; 359/196

(56) References Cited

U.S. PATENT DOCUMENTS

| | | |
|---|---|---|
| 4,728,591 A | 3/1988 | Clark et al. |
| 5,106,729 A | 4/1992 | Lindsay et al. |
| 5,138,174 A | 8/1992 | Tang |
| 5,143,854 A | 9/1992 | Pirrung et al. |
| 5,314,829 A | 5/1994 | Coles |
| 5,346,683 A | 9/1994 | Green et al. |
| 5,363,697 A | 11/1994 | Nakagawa |
| 5,372,930 A | 12/1994 | Colton et al. |
| 5,384,261 A | 1/1995 | Winkler et al. |
| 5,440,122 A | 8/1995 | Yasutake |
| 5,443,791 A | 8/1995 | Cathcart et al. |
| 5,445,934 A | 8/1995 | Fodor et al. |
| 5,445,971 A | 8/1995 | Rohr |
| 5,453,970 A | 9/1995 | Rust et al. |
| 5,467,642 A | 11/1995 | Hosaka et al. |
| 5,472,881 A | 12/1995 | Beebe et al. |
| 5,482,601 A | 1/1996 | Ohshima et al. |
| 5,514,540 A | 5/1996 | Teoule et al. |
| 5,514,550 A | 5/1996 | Findlay et al. |
| 5,519,212 A | 5/1996 | Elings et al. |
| 5,532,128 A | 7/1996 | Eggers et al. |
| 5,571,639 A | 11/1996 | Hubbell et al. |
| 5,601,982 A | 2/1997 | Sargent et al. |
| 5,604,097 A | 2/1997 | Brenner |
| 5,620,854 A | 4/1997 | Holzrichter et al. |
| 5,666,190 A | 9/1997 | Quate et al. |
| 5,670,322 A | 9/1997 | Eggers et al. |
| 5,688,486 A | 11/1997 | Watson et al. |

(Continued)

FOREIGN PATENT DOCUMENTS

| | | |
|---|---|---|
| JP | 06124680 | 5/1994 |
| WO | WO 92/15709 | 9/1992 |
| WO | WO 96/31775 | 10/1996 |
| WO | WO 97/06420 | 2/1997 |
| WO | WO 97/18326 | 5/1997 |
| WO | WO 98/05920 | 2/1998 |
| WO | WO 98/18959 | 5/1998 |
| WO | WO 99/31267 | 6/1999 |
| WO | WO 00/04382 | 1/2000 |
| WO | WO 00/04389 | 1/2000 |
| WO | WO 00/04390 | 1/2000 |
| WO | WO 00/36136 | 6/2000 |
| WO | WO 00/41213 | 7/2000 |
| WO | WO 00/46406 | 8/2000 |
| WO | WO 01/60316 | 8/2001 |
| WO | WO 01/918555 | 12/2001 |
| WO | WO 03/001633 | 1/2003 |
| WO | WO 03/036767 | 5/2003 |
| WO | WO 03/038033 | 5/2003 |
| WO | WO 03/048314 | 6/2003 |
| WO | WO 03/052514 | 6/2003 |

OTHER PUBLICATIONS

U.S. Appl. No. 09/974,757, filed Apr. 11, 2002, Henderson et al.

U.S. Appl. No. 09/929,865, filed Jun. 20, 2002, Henderson et al.

U.S. Appl. No. 10/179,102, filed Jan. 16, 2003, Henderson et al.

U.S. Appl. No. 10/160,372, filed Nov. 21, 2002, Henderson et al.

U.S. Appl. No. 10/128,727, filed Sep. 5, 2002, Henderson et al.

(Continued)

Primary Examiner—John S. Brusca
(74) Attorney, Agent, or Firm—Michael Best & Friedrich LLP

(57) ABSTRACT

The present invention includes a method and apparatus for the detection of a target material. The method and apparatus includes providing a substrate with a surface and forming a domains of deposited materials thereon. The deposited material can be placed on the surface and bound directly and non-specifically to the surface, or it may be specifically or non-specifically bound to the surface. The deposited material has an affinity for a specific target material. The domains thus created are termed affinity domains or deposition domains. Multiple affinity domains of deposited materials can be deposited on a single surface, creating a plurality of specific binding affinity domains for a plurality of target materials. Target materials may include, for example, pathogens or pathogenic markers such as viruses, bacteria, bacterial spores, parasites, prions, fungi, mold or pollen spores. The device thus created is incubated with a test solution, gas or other supporting environment suspected of containing one or more of the target materials. Specific binding interactions between the target materials and a particular affinity domain occurs and is detected by various methods.

40 Claims, 8 Drawing Sheets

U.S. PATENT DOCUMENTS

| | | |
|---|---|---|
| 5,720,928 A | 2/1998 | Schwartz |
| 5,744,305 A | 4/1998 | Fodor et al. |
| 5,753,088 A | 5/1998 | Olk |
| 5,760,300 A | 6/1998 | Kajimura |
| 5,763,768 A | 6/1998 | Henderson et al. |
| 5,789,167 A | 8/1998 | Konrad |
| 5,800,992 A | 9/1998 | Fodor et al. |
| 5,837,832 A | 11/1998 | Chee et al. |
| 5,840,862 A | 11/1998 | Bensimon et al. |
| 5,846,724 A | 12/1998 | Bensimon et al. |
| 5,851,769 A | 12/1998 | Gray et al. |
| 5,866,328 A | 2/1999 | Bensimon et al. |
| 5,866,434 A | 2/1999 | Massey et al. |
| 5,874,219 A | 2/1999 | Rava et al. |
| 5,874,668 A | 2/1999 | Xu et al. |
| 5,958,701 A | 9/1999 | Green et al. |
| 5,965,133 A | 10/1999 | Cantor et al. |
| 5,981,733 A | 11/1999 | Gamble et al. |
| 5,985,356 A | 11/1999 | Schultz et al. |
| 5,992,226 A | 11/1999 | Green et al. |
| 5,993,627 A | 11/1999 | Anderson et al. |
| 6,004,617 A | 12/1999 | Schultz et al. |
| 6,024,925 A | 2/2000 | Little et al. |
| 6,033,911 A | 3/2000 | Schultz et al. |
| 6,045,671 A | 4/2000 | Wu et al. |
| 6,080,586 A | 6/2000 | Baldeschwieler et al. |
| 6,083,763 A | 7/2000 | Balch |
| 6,087,274 A | 7/2000 | Tonucci et al. |
| 6,110,426 A | 8/2000 | Shalon et al. |
| 6,123,819 A | 9/2000 | Peeters |
| 6,143,574 A | 11/2000 | Karlsson et al. |
| 6,146,899 A | 11/2000 | Porter et al. |
| 6,159,742 A | 12/2000 | Lieber et al. |
| 6,171,797 B1 | 1/2001 | Perbost |
| 6,180,114 B1 | 1/2001 | Yager |
| 6,200,737 B1 | 3/2001 | Walt et al. |
| 6,203,814 B1 | 3/2001 | Fisher et al. |
| 6,214,552 B1 | 4/2001 | Heroux et al. |
| 6,218,122 B1 | 4/2001 | Friend et al. |
| 6,231,744 B1 | 5/2001 | Ying et al. |
| 6,232,706 B1 | 5/2001 | Dai et al. |
| 6,239,273 B1 | 5/2001 | Pease et al. |
| 6,255,469 B1 | 7/2001 | Seeman et al. |
| 6,270,946 B1 | 8/2001 | Miller |
| 6,278,231 B1 | 8/2001 | Iwasaki et al. |
| 6,284,497 B1 | 9/2001 | Sabanayagam et al. |
| 6,287,850 B1 | 9/2001 | Besemer et al. |
| 6,289,717 B1 | 9/2001 | Thundat et al. |
| 6,309,831 B1 | 10/2001 | Goldberg et al. |
| 6,329,209 B1 | 12/2001 | Wagner et al. |
| 6,331,396 B1 | 12/2001 | Silverman et al. |
| 6,350,609 B1 | 2/2002 | Morozov et al. |
| 6,395,554 B1 | 5/2002 | Regan et al. |
| 6,406,921 B1 | 6/2002 | Wagner et al. |
| 6,416,952 B1 | 7/2002 | Pirrung et al. |
| 6,420,105 B1 | 7/2002 | Landfield et al. |
| 6,436,647 B1 | 8/2002 | Quate et al. |
| 6,518,168 B1 | 2/2003 | Clem et al. |
| 6,573,369 B2 | 6/2003 | Henderson et al. |
| 2002/0042081 A1 | 4/2002 | Henderson et al. |
| 2002/0063212 A1 | 5/2002 | Mirkin et al. |
| 2002/0076927 A1 | 6/2002 | Henderson et al. |
| 2002/0114987 A1 | 8/2002 | Oscarsson et al. |
| 2002/0122873 A1 | 9/2002 | Mirkin et al. |
| 2002/0123135 A1 | 9/2002 | Henderson et al. |
| 2002/0146714 A1 | 10/2002 | Lieber et al. |
| 2002/0172943 A1 | 11/2002 | Henderson et al. |
| 2002/0179434 A1 | 12/2002 | Dai et al. |
| 2003/0013111 A1 | 1/2003 | Henderson et al. |

OTHER PUBLICATIONS

U.S. Appl. No. 09/574,519, filed Jun. 2003, Henderson et al.

"Microbeam Mass Spectrometry" *Chemical Science and Technology Laboratory, Surface and Microanalysis Science Division* http://www.cstl.nist.gov/div837/Division/expertise/ions/masspecl.htm Jul. 18, 2002.

Abstracts of Papers Part I, 214$^{th}$ "Abstract 027" *ACS National Meeting American Chemical Society,* Sep. 1997, 2 pgs.

Allison, D., et al., "Direct atomic force microscopy imaging of EcoRI endonuclease site specifically bound to plasmid DNA molecules" *PNAS USA,* 1996, 93:8826–8829.

Allison, D., et al., "Mapping Individual Cosmid DNAs by Direct AFM Imaging" *Genomics,* 1997, 41:379–384.

Alves, et al., Atomic scale imaging of alkanethiolate monolayers at gold surfaces with atomic force microscopy: *J. Am. Chem. Soc.,* Feb. 1992, 114(4):1222–1227.

Amro, et al., "Patterning surfaces using tip–directed displacement and self–assembly" *Langmuir,* 2000, 16:3006–3009.

Anwander, et al., "Surface characterization and functionalization of MCM–41 silicas via silazane silylation" *J. Phys. Chem. B.,* 2000, 104:3532–3544.

Arntz, et al., "Label–free protein assay based on a nanomechanical cantilever array" *Nanotechnology,* 14 (2003) 86–90.

Ausubel, F.M., et al. "Current Protocols in Molecular Biology" 1993 ed. vol. 1&2, 1993, Green Publishing Associates and Wiley–Interscience. Table of contents only.

Collins, et al., "Engineering Carbon Nanotubes and Nanotube Circuits Using Electrical Breakdown," Apr. 2001, 292(5517):706–799.

Bailey, C.P., et al., Cationic oligonucleotides can mediate specific inhibition of gene expression in Xenopus oocytes *Nuc. Acids Res.,* 1998, 26(21):4860–4867.

Bain, et al., "Modeling organic surfaces with self–assembled monolayers" *Agnew. Chem. Int. Ed. Engl.,* 1989, 28(4):506–512.

Baselt, D.R., et al., "A biosensor based on magnetoresistance technology" *Biosens. Bioelectorn,* 1998, 13(7–8):731–739.

Bedouelle, H., "Reagentless fluorescent Immunosensors" *Antibody Engineerings,* IBC's 13$^{th}$ International Conference, Dec. 2, 2002.

Belaubre, P. et al., "Fabrication of biological microarrays using microcantilevers" *Applied Physics Letters,* May 5, 2003, 82(18):3122–3124.

Bensimon, A., et al., "Alignment and sensitive detection of DNA by a moving interface" *Science,* Sep. 30, 1994; 265(5181):2096–2098 [PMID 7522347] Abstract.

Berggren, et al., "Microlithography by using neutral metastable atoms and self–assembled monolayers" *Science,* Sep. 1995, 269(5228):1255–1257.

Bernard, et al. "Printing patterns of proteins" *Langmuir The ACS Journal of Surfaces and Colliod,* Apr. 1998, 14(9):2225–2229.

Binggeli, et al., "Influence of capillary condensation of water on nanotribology studied by force microscopy" *Appl. Phys. Lett.,* Jul. 1994, 65(4):415–417.

Binning, et al., "Surface studies by scanning tunneling microscopy" *Phys. Rev. Lett.,* 1982, 49(1):57–61.

Binning, G., et al., Atomic force microscope *Phys. Rev. Lett.,* 1986, 56(9):930–933.

Bishop, et al., "Self–assembled monolayers: recent developments and applications" *Colloid & Interface Science,* Feb. 1996, 1:127–136.

Bottomley, L., "Scanning probe microscopy" *Anal. Chem.,* Jun. 1998, 70(12):425R–475R.

Brandow, S., et al., "Metal pattern fabrication using the local electric field of conducting atomic force microscope probe" *J. Vac. Sci. Technol.,* May/Jun. 1997, 15(3):1455–1459.

Brenner, S., et al., "Gene expression analysis by massively parallel signature sequencing (MPSS) on microbead arrays" *Nat. Biotechnol 2000,* Jun. 18(6):630–634, 2000.

Brody, E., and Gold, L., "Aptamers as therapeutic and diagnostic agents" *Molecular Biotechnology,* 2000, 74:5–13.

Bruckbauer, et al., "Writing with DNA and Protein Using a Nanopipet for Controlled Delivery" *JACS,* 2002, A–B.

Bulyk, et al., "Quantifying DNA–protein interactions by double–stranded DNA arrays" *Nature Biotechnology,* Jun. 1999, 17:573–577.

Bustamante C., et al., "Circular DNA Molecules Imaged in Air by Scanning Force Microscopy" *Biochemistry,* 1992, 31:22–26.

Bustamante, C., et al., "Biochemical and structural applications of scanning force microscopy" *Curr. Opin. Struct. Biol.,* 1994 4(5):750–760.

Carr, et al., "High–selectivity pattern transfer process for self–assembled monolayer electron beam resists" *J. Vac. Sci. Technol.,* May/Jun. 1997, 15(3):1446–1450.

Cheng, et al., "Preparation and hybridization analysis of DNA/RNA from *E. coli* on microfabricated bioelectronic chips" *Nature Biotechnology,* 1998, 16:541–546.

Chrisey et al, "Fabrication of patterned DNA surfaces" *Nucleic Acids Research,* (Oct. 1996)24(15):3040–3047.

Clark, M.W. et al., "Nanotechnology tools for functional proteomics analysis" *American Biotechnology Laboratory,* Mar. 2001, 16–18.

Colas, et al., "Genetic selection of peptide aptamers that recognize in inhibit cyclin–dependent kinase 2", *Nature,* Apr. 1996 380(11):548–550.

Colvin, et al. "Semiconductor nanocrystals covalently bound to metal surfaces with self–assembled monolayers" *J. Am. Chem. Soc.,* 1992, 114:5221–5230.

Cui, Y, et al., "Nanowire nanosensors for highly sensitive and selective detection of biological and chemical species" *Science,* 2001, 293, 1289–1292.

Dai, et al., "Nanotube Molecular Wires as Chemical Sensors" *Science,* Jan. 28, 2000, 287:622–625.

Dai, H, et al., "Controlled chemical routes to nanotube architectures" Physics and Devices, *J. Phys. Chem B,* 1999, 103:11246–11255.

Dai, H, et al., "Probing electrical transport in nanomaterials: conductivity of individual carbon nanotubes" *Science,* 1996, 272(5261):523–526.

Dammer, et al., "Binding strength between cell adhesion proteoglycans measured by atomic force microscopy" *Science,* 1995, 267:1173–1175.

Dammer, et al., "Specific antigen/antibody interactions measured by force microscopy" *Biophys. J.,* 1996, 70:2437–2441.

Delamarch, E., et al., "Patterned delivery of immunoglobulins to surfaces using microfluidic networks" *Science,* 1997, 276:779–781.

Ding, Y., Oka, T., et al., "Near–field stimulated TOF nanometric surface mass spectroscopy: characterization of Nano–localized surfaces" Joint International Meeting—200th Meeting of the Electrochemical Society, Inc., 52nd Annual Meeting of the International Society of Electrochemistry, San Francisco, California (2001).

Ding, Y., Ruggero, M. et al., "Development of UHV–STM/TOF hybrid mass analyzer system for nano–characterization of metal silicide surfaces" 198th Meeting of the Electrochemical Society, Phoenix, Arizona (2000).

DeRisi, et al., "Exploring the Metabolic and Genetic Control of Gene Expression on a Genomic Scale" *Science,* Oct. 1997, 278:680–686.

Dong, Y. and Shannon, C., "Heterogeneous Immunosensing Using Antigen and Antibody Monolayers on Gold Surfaces with Electrochemical and Scanning Probe Detection" *Anal. Chem.,* 2000, 72:2371–2376.

Dontha, N., et al., "Development of sub–micron patterned carbon electrodes for immunoassays" *J. Pharm. Biomed. Analysis,* (Feb. 1999) 19:83–91.

Dontha, N., et al., "Generation of Biotin/Avidin/Enzyme Nanostructures with Maskless Photoligography" *Anal. Chem.,* 1997, 69: 619–2625.

Dubois, L. et al., "Synthesis, Structure, and Properties of Model Organic Surfaces" *Annu. Rev. Phys. Chem.,* 1992, 43:437–463.

Durbin, S., Feher, G., "Protein crystallization" *Annual Review of Phys Chemistry,* 1996, 47:171–204.

Falvo, M.R., et al., "Bending and buckling of carbon nanotubes under large strain" *Nature,* 1997, 389:582–584.

Fan, S., et al., "Self–oriented regular arrays of carbon nanotubes and their functional devices" *Science,* 1999, 283, 512.

Fang, et al., "Membrane Protein Microarrays" *JACS,* 2002, 124(11):2394–2395.

Farajian, A.A., "Nanolinear Coherent Transport Through Doped Nantube Junctions" *Physical Review,* Jun. 21, 1999, 82(25):5084–5087.

Feigon, J. "DNA triplexes, quadruplexe, and aptamers" *Clin. Chem.,* 1994, 40(4):647–647.

Florin, E., et al., "Adhesion forces between individual ligan–receptor pairs" *Science,* 1994, 264:415–417.

Fodor, S., et al., "Light–directed spatially addressable parallel chemical synthesis" *Science* 1991, 251: 767–773.

Fodor, S., et al., "Multiplexed biochemical assays with biological chips" *Nature,* 1993, 364:555–557.

Frisbie, C.D. et al., "Functional group imaging by chemical force microscopy" *Science,* 1994, 265:2071–2074.

Fritz, J., et al., "Translating biomolecular recognition into nanomechanics" *Science,* 2000, 316–318.

Fritzsche, W., et al., "Application of Atomic Force Microscopy to Visualization of DNA, Chromatin and Chromosomes" *Critical Reviews™ in Eukaryotic Gene Expression,* 1997, 7(3):231–240.

Fritzsche, W., et al., "Chicken Erythrocyte Nucleosomes Have a Defined Orientation along the Linker DNA–A Scanning Force Microscopy Study" *Scanning,* 1997, 19:42–47.

Fritzsche, W., et al., "Mapping elasticity of rehydration metaphase chromosomes by scanning force microscopy" *Ultramicroscopy,* 1997, 69:191–200.

Fritzsche, W., et al., "Ribosomes substructure investigated by scanning force microscopy and image processing" *Journal of Microscopy,* 1998, 189, Pt 1, 50–56.

Fujihira, et al., "Effect of capillary force on friction force microscopy: a scanning hydrophilicity microscope" *Chemistry Letters,* Jul. 1996, 7:499–500.

Gillen, G., Bennett, J., et al., "Molecular imaging secondary ion mass spectrometry for the characterization of patterned self–assembled monolayers on silver and gold" *Anal. Chemistry,* 1994, 66:2170–2174.

Girault, S., Chassaing, G. et al, "Coupling of MALDI–TOF mass analysis to the separation of biotinylated peptides by magnetic streptavidin beads" *Anal. Chemistry* 1996, 68:2122–2126.

Grabar, et al., "Preparation and characterization of Au colloid monolayers" *Anal. Chem.,* 1995, 67(4):735–743.

Haab, et al., "Protein microarrays for highly parallel detection and quantitation of specific proteins and antibodies in complex solutions" *Genome Biology,* 2001, 2(2)0004.1–0004.13.

Hansma, H.G., et al., "Atomic force microscopy of long and short double–stranded, single–stranded, and triple–stranded nucleic acids" *Nuc. Acids Res.,* 1996, 24(4):713–720.

Hansma, H.G., et al., "Recent advances in atomic force microscopy of DNA" *Scanning* 1993, 15(5):296–9.

Hansma, H.G., Sinsheimer, R.L., et al., "Atomic force microscopy of single–and double–stranded DNA" *Nucleic Acids Research* 1992, 20:3585–90.

Hansma, P.K., et al., "Tapping mode atomic force microscopy in liquids" *Appl. Phys. Lett.,* 1994, 64(13):1738–1740.

Heller, et al., "Discovery and analysis of inflammatory disease–related genes using cDNA microarrays" *PNAS USA,* 1997, 94: 2150–2155.

Henderson, E., "Atomic force microscopy of conventional and unconventional nucleic acid structures" *Journal of Microscopy,* 1992, 77–84.

Henderson, E., "Imaging and nanodissection of individual supercoiled plasmids by atomic force microscopy" *Nuc. Acids Res.,* 1992, 20(3):445–447.

Henderson, E., "Imaging of Living Cells by Atomic Force Microscopy" *Progress in Surface Science,* May 1994, 46(1):39–60.

Henderson, E., "Molecular force detection and spectroscopy with the atomic force microscope" *Science Progress,* 1998, 81(2):141–151.

Henderson, E., et al., "Actin Filament Dynamics in Living Glial Cells Imaged by Atomic Force Microscopy" *Science,* 1992, 257:1944–1946.

Henderson, E., et al., "New Ribosome Structure" *Science,* 1984, 255:510–512.

Henderson, E., et al., "Telomeric DNA oligonucleotides form novel intramolecular structures containing guanine–guanine base pairs" *Cell,* 51(6):899–908.

Henderson, et al., "A method for gold coating experimental detector beampipes" httb://www.Ins.cornell.edu/public/CBN/1999/CBN99–7/cbn99–7.pdf, 1999.

Hiller, et al., "Microarrayed allergen molecules: diagnostic gatekeepers for allergy treatment" *FASEB,* 2002, 16:414–416.

Hinterdorfer, P. et al., "Detection and localization of individual antibody–antigen recognition events by atomic force microscopy" *PNAS,* 1996, 93:3477–3481.

Hoh, J.H. and Hansma, P.K., "Atomic force microscopy for high resolution imaging in cell biology" *Trends in Cell Biology,* 1992, 2:208–213.

Hoh, J.H., et al., "Atomic force microscopy and dissection of gap junctions" *Science,* 1991, 1405–1408.

Hoh, J.H., et al., "Quantized adhesion detected with the atomic force microscope" *J. Am. Chem. Soc.,* 1992, 114:4917–4918.

Hong, et al., "A new tool for studying the in situ growth processes for self–assembled monolayers under ambient conditions" *Langmuir,* 1999, 15:7879–7900.

Hong, et al., "Multiple ink nanolithography: toward a multiple–pen nano–plotter" *Science,* 1999, 286:523–525.

Hong, S. et al. "A Nanoplotter with Both Parallel and Serial Writing Capabilities" *Science,* Jun. 9, 2000, 288:1808–1811.

Hovis, et al., "Cyloaddition chemistry and formation of ordered organic monolayers on silicone (001) surfaces" *Surface Science,* 1998, 402–404, pp. 1–7.

Hovis, et al., "Structure and bonding of ordered organic monolayers of 1,5–cyclooctadiene on the silicon (001) Surface" *J. Phys. Chem. B.,* 1997, 101:9581–9585.

Hu, et al., "Imaging the condensation and evaporation of molecularly thin films of water with nanometer resolution" *Science,* 1995, 268(5208):267–269.

Huck, et al., "Patterned polymer multilayers as etch resists" *Langmuir,* 1999, 15:6862–6867.

Ivanisevic, et al., "Dip–Pen Nanolithography on Semiconductor Surfaces" *J. Am. Chem. Soc.,* 2001, 123:7887–7889.

Iyer, et al., "The Transcription Program in the Response of Human Fibroblasts to Serum" *Science,* 1999, 283(5398):83–87.

Jackman, et al., "Fabrication of submicrometer features on curved substrates by microcontact printing" *Science,* 1995, 269: 664–666.

James, et al., "Patterned protein layers on solid substrates by thin stamp microcontact printing" *Langmuir,* 1998, 14:741–744.

Janes, et al., "Electronic conduction through 2D arrays of nanometer diameter metal clusters" *Superlattices and Microstructures,* 1995, 18(4):275–282.

Jaschke, et al., "Deposition of organic material by the tip of a scanning force microscope" *Langmuir,* 1995, 11:1061–1064.

Jin, X., Unertl, W., "Submicrometer modification of polymer surfaces with a surface force microscope" *Applied Physics Letters,* 1992, 61(6):657–659.

Jones, V., et al., "Microminiaturized Immunoassays Using Atomic Force Microscopy and Compositionally Patterned Antigen Arrays 66" *Anal. Chem.,* 1998, 70(7):1233–1241.

Karpovich, et al., "Direct measurement of the adsorption kinetics of alkanethioilate self–assembled monolayers on microcrystalline gold surface" *Langmuir,* 1994, 10:3315–3322.

Kim, et al., "Nanotube nanotweezers" *Science,* Dec. 10, 1999, 286:2148–2150.

Knezevic et al., "Proteomic profiling of the cancer microenvironment by antibody arrays" *Proteomics,* 2001,. 1:1271–1278.

Kochanek, et al., "Transciptional silencing of human ALU sequences and inhibition of protein binding in the box B regulatory elements by 5'CG3 methylation" *FEBS Lett.,* 1995, 360(2):115–120 [PMID 7875314] Abstract.

Komeda, et al., "Octadecyltrichlorosilane self–assembled–monolayer islands as a self–patterned–mask for HF etching of $SiO_2$ on Si" *J. Vac. Sci. Technol A.,* 1998, 16(3):1680–1685.

Kumar, et al., "The use of self–assembled monolayers and a selective etch to generate patterned gold features" *J. Am. Chem. Soc.,* 1992, 114:9188–9189.

Lahiri, et al., "Patterning ligands on reactive SAMs by microcontact printing" *Langmuir*, 1999, 15:2055–2060.

Laibinis et al., "ω–terminated alkanethiolate monolayers on surfaces of copper, silver, and gold have similar wettabilities[1]" *J. Am. Chem. Soc.*, 1992, 114: 1990–1995.

Lal, R. and John, S.A., "Biological applications of atomic force microscopy" *Am J. Physiology*, 1994, 266(1):1–21.

Lanio, T., et al., "PCR–based random mutagenesis method using spiked oligonucleotides to randomize selected parts of gene without any wild–type background" *Biotechnique*, 1998, 25(6):958–965.

Lee, et al., "Nanometer–scale lithography on H–passivated Si(100) by atomic force microscope in air" *J. Vac. Sci. Technol. A.*, 1997, 15(3):1451–1454.

Lee, G. et al., "Direct measurement of the forces between complementary strands of DNA" *Science*, 1994, 266:771–773.

Lercel, et al. "Self–assembled monolayer electron–beam resists on GaAs and $SiO_2$," *J. Vac. Sci. Technol. B.*, 1993, 11(6): 2823–2828.

Lercel, et al., "Sub–10nm lithography with self–assembled monolayers" *Appl. Phys. Lett.*, 1996, 68(11):1504–1506.

Liu, et al., "Nanofabrication of self–assembled monolayers using scanning probe lithography" *Acc. Chem. Res.*, 2000, 33(7):457–466.

Lo, et al., "Organic and inorganic contamination on commercial AFM cantilevers" *Langmuir*, 1999, 15:6522–6526.

Lüthi, et al., Parallel nanodevice fabrication using a combination of shadow mask and scanning probe methods: *Applied Physics Letters*, 1999, 75(9):1314–1316.

Lutwyche, et al., "5X5 2D AFM cantilever arrays a first step toward Terabit storage device" *Sensors and Actuators*, 1999, 73:89–94.

Lynch, M., et al., "A Reliable Preparation Method for Imaging DNA by AFM" *Microscopy Today*, 1999, 99(9) 1 pg.

Lyubchenko, Y.L., et al., "Atomic force microscopy of DNA and bacteriophage in air, water and propanol: The role of adhesion forces" *Nuc. Acids Res.*, 1993, 21(5):1117–1123.

Macaya, et al., "Thrombin–binding DNA aptamer forms a unimolecular quadruplex structure in solution" *PNAS USA*, Apr. 1993, 90:3745–3749.

MacBeath, G. and Schreiber, S.L., "Printing Proteins as Microarrays for High–Throughput Function Determination" *Science*, Sep. 8, 2000, 289:1760–1763.

Magno, R., Bennett, B., "Nanostructure patterns written in III–V semiconductors by an atomic force microscope" *Applied Physics Letters*, 1997, 70(14):1855–1857.

Malmborg, et al., "Real Time Analysis of Antibody–Antigen Reaction Kinetics", *Scand. J. Immunol.*, 1992, 35:634–650.

Marsh, T.C., et al., "A new DNA nanosctructure imaged by scanning probe microscopy" *Nuc. Acids Res.* 1995, 23(4):696–700.

Marsh, T.C., et al., "G–wires: Self–assembly of a telometic oligonucleotide, d(GGGGTTGGGG), into large superstructures" *Biochemistry* 1994, 33:10718–10724.

Martin, B., et al., "Ortogonal Self–Assembly on Colloidal Gold–Platinum Nanorods" *Advanced Materials*, 1999, 11:1021.

Matteucci, et al., "Synthesis of deoxyoligonucleotides on a polymer support 1" *J. Am. Chem. Soc.*, 1981, 103:3185–3191.

Maynor, et al., "Au :Ink" for AFM "Dip–Pen" Nanolithography *Langmuir*, 2001, 17:2575–2579.

Mazzola, L., "Discrimination of DNA hybridization using chemical force microscopy" *Biophysical Journal*, 1999, 76:2922–2933.

Mazzola, L., "Imaging biomolecule arrays by atomic force microscopy" *Biophysical Journal*, 1995, 68:1653–1660.

Fuhrer, et al., "Crossed nanotube Junctions" *Science*, Apr. 21, 2000, 288:494–497.

Meister, et al., "Nanoscale Dispensing of Liquids through Cantilevered Probes" *MNE '02*, Lugano, Switzerland, Sep. 16–19, 2002.

Mendoza, et al., "High–Throughput Microarray–Based Enzyme–Linked Immunosorbent Assay (ELISA)" *BioTechniques*, 1994, 27(4):778–788.

Meyer, G. and N.M. Amer, "Novel optical approach to atomic force microscopy" *Appl. Phys. Lett.*, 1988, 53:1045–1047.

Minne, et al., "Centimeter scale atomic force microscope imaging and lithography" *Applied Physics Letters*, 1998, 73(12):1742–1744.

Minne, S.C., et al., "Automated parallel high–speed atomic force microscopy" *Appl. Phys. Lett.*, 1998, 72(18):2340–2342.

Mirkin, et al., "Dip–Pen Nanolithography: Controlling Surface Architecture on the Sub–100 Nanometer Length Scale" *Chemphyschem*, 2001, 2:37–39.

Mirkin, et al., "Programming the Assembly of Two– and Three–Dimensional Architectures with DNA and Nanoscale Inorganic Building Blocks" Invited Contribution from Recipient of ACS Award in Pure Chemistry *Inorg. Chem.*, 2000, 39:2258–2272.

Mosher, C., et al., "NanoArrays, The Next Generation Molecular Array Format for High Throughput Proteomics, Diagnostics and Drug Recovery" *JALA*, 2000, 5(5):75–83.

Moy, et al., "Intermolecular Forces and Energies Between Ligands and Receptors" *Science*, 1994, 266:257–259.

Moy, V.T., et al., "Probing the forces between complimentary strands of DNA with the atomic force microscope" *SPIE*, 1995, 2384:2–12.

Mueller, et al., "Atomic force microscopy deposition of poly–l–lysine structures onto lipid bilayers supported by mica" *Langmuir*, 2000, 16:9568–9570.

Müller, et al., "Nanostructuring of alkanethiols with ultrastrap field emitters" *J. Vac. Sci. Technol. B.*, 1995, 13(6):2846–2849.

Murray, et al., "Atomic force microscopy of biochemically tagged DNA" *Proc., Natl., Acad. Sci.*, 1993, 90:3811–3814.

Musil, C., Nanostructuring of gold electrodes for immunosensing applications: *J. Vac. Sci. Technol. B.*, 1995, 13(6):2781–2786.

Niu, et al., "Atomic force microscopy of DNA–colloidal gold and DNA–protein complexes" *SPIE Advances in DNA Sequencing Technology*, 1993, 1891:71–77.

Noy, et al., "Chemical force microscopy: exploiting chemically–modified tips to quantify adhesion, friction, and functional group distributions in molecular assemblies" *J. Am. Chem.*, 1995, 117:7943–7951.

Noy, et al., "Chemically–sensitive imaging in tapping mode by chemical force microscopy: relationship between phase lag adhesion" *Langmuir*, 1998, 14:1508–1511.

Nuzzo, R., "Spontaneously organized molecular assemblies. 3. Preparation and properties of solution adsorbed monolayers of organic disulfides on gold surfaces" *J. Am. Chem. Soc.*, 1987, 109:2358–2368.

Nyffenegger, et al., "Nonometer scale surface modification using the scanning probe microscope: progress since 1991" Chem. Rev., 1997, 97:1195–1230.

O'Brien, J., et al., "Immunosensing Platforms Using Spontaneously Absorbed Antibody Fragments on Gold" Analytical Chemistry, 2000, 72(4)703–710 [PMID 10701253] Abstract.

Oshio, T. et al., "Atomic force microscopy detection system using an optical fiber heterodyne interferometer free from external disturbances" Ultramicroscopy 42–44 (Jul. 1992) 310–314.

Paweletz, et al., "Reverse phase protein microarrays which capture disease progression shoe activation of pro–survival pathways at the cancer invasion front" Oncogen, 2001, 20:1981–1989.

Pawlak, et al., "Zeptosens' protein microarrays: A novel high performance microarray platform for low abundance protein analysis" Proteomics, 2002,. 2:383–393.

Perkins, et al., "Fabrication of 15 nm wide trenches in Si by vacuum scanning tunneling microscope lithography of an organosilane self–assembled film and reactive ion etching" Appl. Phys. Lett., 1996, 68(4):550–552.

Pfannschmidt, et al., "Sequence–specific labeling of superhelical DNA by triple helix formation and psoralen crosslinking" Nucleic Acids Research, 1996 24(9):1702–1709.

Piner, et al., "Improved imaging of soft materials with modified AFM tips" Langmuir, 1999, 15:5457–5460.

Piner, R.D., et al., "Dip–Pen Nanolithography" Science, Jan. 29, 1999,283(5402):661–663.

Piner, Richard, "Effect of water on lateral force microscopy in air" Langmuir, 1997, 13:6864–6868.

Putnam, C.A.J., "Tapping atomic force microscopy in liquids" Appl. Phys. Lett., 1994, 64(18):2454–2456.

Qin, et al., Fabrication of ordered two–dimensional arrays of micro– and nanoparticles using patterned self–assembled monolayers as templates: Adv. Matter, 1999, 11(17):1433–1437.

Rankin, P.C. Wilson, A.T. "The Surface Chemistry of the Mica–Aluminum–Sulfate System" Journal of Colloid and Interface Science, (1969) 30(3):277–282.

Reed, et al., "Conductance of molecular junction" Science, 1997, 278:252–254.

Rief, et al., "Reversible unfolding of individual Titin Ig–domains by AFM" Science, 1997, 276:1109–1111.

Rief, M., et al., "Single Molecule Force Spectroscopy on Polysaccharides by Atomic Force Microscopy" Science, 1997, 275:1295–1297.

Rief, M., et al., "The mechanical stability of immunoglobulin and fibronectin III domains in the muscle protein titin measured by atomic force microscopy" Biophysical Journal, 1998, 3008–3014.

Robinson, et al., Autoantigen microarrays for multiplex characterization of autoantibody responses Nature Medicine, Mar. 2002, 8(3):1–7.

Santos, et al., "Probing hydrophobic interactions of surfaces and macromolecules with atomic force microscope" Book of Abstracts, 214 ACS National meeting, Sep. 7–11, 1997, PHYS–248.

Sastry, et al., "Formation of patterned hetrocolloidal nanoparticle thin films" Langmuir, 2000, 16:3553–3556.

Schaus, S., et al., "Cell Viability and Probe–Cell Membrane Interactions of XR1 Glial Cells Imaged by Atomic Force Microscopy" Biophysical Journal, Sep. 1997, 73:1205–1214.

Schena, et al., "Parallel human genome analysis: Microarray–based expression monitoring of 1000 genes" PNAS USA, 1996, 93:10614–10619.

Schoer, et al., "Scanning probe lithography. 4. Characterization of scanning tunneling microscope–induced patterns in n–Alknethiol self–assembled monolayers" Langmuir, 1997, 13:2323–2332.

Schumacher, et al., "Nanomachining of mesoscopic electronic devices using an atomic force microscope" Applied Physics, 1999, 75(8):1107–1109.

Schwartz, et al. "Meniscus Force Nanografting: Nanoscopic Patterning of DNA" Langmuir, 2001, 17:5971–5977.

Schwartz, et al., "Molecular Transport from an Atomic Force Microscope Tip: A Comparative Study of Dip–Pen Nanolithography" Langmuir, American Chemical Society, Nov. 6, 2001.

Schweitzer, et al., "Multiplexed protein profiling on microarrays by rolling–circle amplification" Nature Biotechnology, Apr. 2002, 20:359–365.

Shaiu, W.L., et al., "Atomic Force Microscopy of Oriented Linear DNA Molecules Labeled with 5nm Gold Spheres" Nuc. Acids Res., 1993, 21(1):99–103.

Shaiu, W.L., et al., "Visualization of circular DNA molecules labeled with colloidal gold spheres using atomic force microscopy" J. Vac. Sci. Technol. A., 11(4):820–823.

Sheehan, et al., "Thiol diffusion and the role of humidity in "dip pen" nanolithography" Physical Review Letters, Apr. 15, 2002, 88(15):156104–1–56104–4.

Sheen, et al., "A new class of organized self–assembled monolayers: alkane thiols on GaAs (100)" J. Am. Chem. Soc., 1992, 114:1514–1515.

Sherman, Chemical Vapor Deposition For Microelectornices: Principles, Technology and Applications (Noyes, Park Ridges, NJ, 1987). (Book Reference Not Being Provided).

Shlyakhtenko, L.S., et al., "Structure and dynamics of supercoil–stabilized DNA cruciforms" J. Mol. Biol., 1998, 280(1):61–72.

Shlyakhtenko, L.S., Gall, A.A., et al., "Atomic force microscopy imaging of DNA covalently immobilized on a functional mica substrate" Biophysical Journal, Jul. 1999, 77:568–576.

Silzel, et al., "Mass–sensing, multianalyte microarray immunoassay with imaging detection" Clinical Chemistry, 1998, 44(9):2036–2043.

Collins, et al., "Nanotube Device" Science, Oct. 3, 1997, 278:100–103.

Smith et al., "Overstretching B–DNA: the elastic response of individual double–stranded and single stranded DNA molecules" Science, Feb. 9, 1996, 271:795–799.

Snow, et al., "High speed patterning of a metal silicide using scanned probe lithography" Applied Physics Letters, 1999, 75(10):1476–1478.

Soh, H., et al., "Integrated nanotube circuits: controlled growth and ohmic contacts to single–walled–carbon nanotubes" Appl. Phys. Lett., 1999, 75(5): 627–629.

Sondag–Huethorst, et al., "Generation of electrochemically deposited metal patterns by means of electron beam (nano) lithography of self–assembled monolayer resists" Appl. Phys. Lett. 1994, 64(3):285–287.

Southern, E.M., "Detection of specific sequences among DNA fragments separated by gel electrophoresis" *J. Mol. Biol.* 1975, 98:503–517.

Spectroscopy Europe—News Feb./Mar. 2002, 6 pages, http://www.spectroscopyeurope.com/news14_1.html.

Spence, J., Weierstall, U., et al., "Atomic species identification in scanning tunneling microscopy by time of flight spectroscopy" *J. Vac. Sci. Tech.,* 1996, B14(3):1587–1590.

Sreekumar, et al., "Profiling of cancer cells using protein microarrays: Discovery of novel radiation–regulated proteins" *Cancer Research,* 2001, 61:7585–7593.

Steiner, et al., "Adsorption of alkanenitriles and alkanedinitriles on gold and copper" *Langmuir,* 1992, 8:2271–2777.

Stöckle, R., Setz, P. "Nanoscale Atmospheric Pressure Laser Ablation–Mass Spectrometry" *Anal. Chem.,* 2001, 73(7):1399–1402.

Su, et al., "Moving beyond Molecules: Patterning Solid–State Features via Dip–Pen Nanolithography with Sol–Based Inks" *JACS,* 2002, 124(8):1560–1561.

Sun, et al., "Nanoscale Molecular Patterns Fabricated by Using Scanning Near–Field Optical Lithography" *JACS,* 2002, 124(11):2414–2415.

Tang, K., Fu, D., et al., "Matrix–assisted laser desorption/ionization mass spectrometry of immobilized duplex DNA probes" *Nucleic Acids Research,* 1995, 23(16):3126–3131.

Tans, et al., "Room–temperature transistor based on a single carbon nanotube" *Nature,* May 7, 1998, 393:49–52.

Tarlov, M.J., Newman, J.G., et al., "Static secondary ion mass spectrometry of self–assembled alkanethiol monolayers on gold" *Langmuir,* 1992, 8:1398–1405.

Tien, et al., "Microfabrication through electrostatic self–assembly" *Langmuir,* 1997, 13:5349–5355.

Troughton, E., Bain, C., et al., "Monolayer films prepared by the spontaneous self–assembly of symmetrical and unsymmetrical dialkyl sulfides from solution onto gold substrates: Structure, properties and reactivity of constituent functional groups" *Langmuir,* 1988, 4:365–385.

Tsukamoto, et al. "Twin–probe scanning tunneling microscope" *Rev. Sci. Instrum.,* Jul. 1991, 62(7):767–1771.

Uetz, P., et al., "A comprehensive analysis of protein–protein interactions in *Saccharomyces cerevisiae*" *Nature,* Feb. 10, 2000, 403(6770):623–627.

Ulman, Abraham, "Formation and structure of self–assembled monolayers" *Chem. Rev.,* 1996, 96:1533–1554.

Vesenka, J. et al., "A substrate preparation for reliable imaging of DNA molecules with the scanning force microscope" *Ultramicroscopy,* 1992, 42–44:1243–1249.

Vesenka, J., et al., "Colloidal gold particles as an incompressable atomic force microscope imaging standard for assessing the compressability of biomolecules" *Biophys. J.,* 1993, 65:992–997.

Vesenka, J., et al., "Combining optical and atomic force microscopy for life sciences research" *BioTechniques,* 1995, 19(2):240–253.

Vettiger, et al., "Ultrahigh density, high–data–rate NEMS–based AFM data storage system" *Microelectronic Engineering,* 1999, 46:11–17.

Vezenov, Dmitri, "Force titrations and ionization state sensitive imaging of functional groups in aqueous solutions by chemical force microscopy" *J. Am. Chem. Soc.,* 1997, 119:2006–2015.

Vossmeyer, et al., "Combinatorial approaches toward patterning nanocrystals" *Journal of Applied Physics,* 1998, 84(7):3664.

Wadu–Mesthrige, et al., "Fabrication and imaging of nanonmeter–sized protein patterns" *Langmuir,* 1999, 15:8580–8583.

Wallraff, et al., "Lithographic imaging techniques for the formation of nanoscopic features" *Chem. Rev.,* 1999, 99:1801–1821.

Walters, D.A., Hampton, A.D., et al. "Atomic force microscope integrated with a scanning electron microscope for tip fabrication" *Applied Physics Letters,* Aug. 8, 1994, 65(6):787–789.

Wang, et al., "Nanometer scale patterning and pattern transfer on amorphous Si, crystalline Si, and $SiO_2$ surfaces using self–assembled monolayers" *Appl. Phys. Lett.,* 1997, 70(12):1593–1595.

Weierstall, U. Spense, J. "Atom species identification in STM using an Imaging Atom–Probe technique" *Surface Science* 1998, 398: 267–279.

Whitesides, et al., "Self–assembled monolayers and lithography" *Nanophase Chemistry* 1995, 39: 109–122.

Wilbur, et al., "Scanning force microscopes can image patterned self–assembled monolayers" *Langmuir,* 1995, 11:825–831.

Williamson, et al., "G–quarters in biology: Riprise" *PNAS USA,* Apr. 15, 1993, 90(8):3124–3124.

Williamson, et al., "Monovalent cation–induced structure of telomeric DNA: The G–quartet model" *Cell,* 1989, 59(5):871–880.

Wilson, et al., "Surface organization and nanopatterning of collagen by dip–pen nanolithography" *PNAS,* Nov. 20, 2001, 98(24):13660–13664.

Wong, S., et al., "Covalently functionalized nanotubes as nanometre–sized probes in chemistry and biolog" *Nature,* 1998, 394:52–55.

Wong, S., et al., "Covalently functionalized single–walled carbon nanotube probe tips for chemical force microscopy" *Journal of the American Chemical Society,* 1998, 120:8557–8558.

Wong, S., et al., "Functionalization of carbon nanotube AFM probes using tip–activated gases" *Chem Physics Letters,* 1999, 306:219–225.

Xia, et al., "A selective etching solution for use with patterned self–assembled monolayers of alkanethiolates on gold" *Chem. Mater.,* 1995, 7:2332–2337.

Xia, et al., "Complex optical surfaces formed by replica molding against elastomeric masters" *Science,* 1996, 273: 347–349.

Xia, et al., "Pattern transfer: self–assembled monolayers as ultrathin resists" *Microelectronic Engineering,* 1996, 32:255–268.

Xia, et al., "Soft lithography" *Agnew Chem. Int. Ed.,* 1998, 37:551–575.

Xia, et al., "Unconventional methods for fabricating and patterning nanostructures" *Chem. Rev.,* 1999, 99:1823–1848.

Xu, et al., "Fabrication of nanometer scale patterns within self–assembled monolayers by nanografting" *Langmuir,* 1999, 15:7244–7251.

Xu, et al., Nanometer–scale fabrication by simultaneous nanoshaving and molecular self–assembly: *Langmuir,* 1997, 13:127–129.

Xu, et al., "Wetting and capillary phenomena of water on mica" *J. Phys. Chem. B.,* 1998, 102:540–548.

Yan Li, et al., "Electrochemical AFM "Dip–Pen" Nanolithography" *J. Am. Chem., Soc.* 2001, 123:2105–2106.

Yan, et al., "Patterning a performed, reactive SAM using microcontact printing" *J. Am. Chem. Soc.,* 1998, 120:6179–6180.

Yan, et al., "Patterning thin films of poly(ethylene imine) on a reactive SAM using microcontact printing" *Langmuir,* 1999, 15:1208–1214.

Ying, et al., "Programmable Delivery of DNA through a Nanopipet" *Anal. Chem.,* 2002, 74:1380–1385.

Youil, R, Screening for mutations by enzyme mismatch cleavage with T4 endonuclease VII *PNAS USA,* 1995, 92(1):87–91.

Zhong, Q., et al., "Fractured polymer/silica fiber surface studied by tapping mode atomic force microscopy" *Surf. Sci. Lett.,* Jan. 3, 1993, 290: L 688–L692.

Zhu, et al., "Analysis of yeast protein kinases using protein chips" *Nature Genetics,* 2000, 26:283–289.

Zhu, et al., "Global Analysis of Protein Activities Using Proteome Chips" *Science,* Sep. 2001, 293(14):2101–2105.

Figure 7a    Figure 7b    Figure 7c

DEVICE AND METHOD OF USE FOR DETECTION AND CHARACTERIZATION OF PATHOGENS AND BIOLOGICAL MATERIALS

CROSS-REFERENCE TO RELATED APPLICATION(S)

This application is a CIP of U.S. application Ser. No. 09/519,271, filed Mar. 7, 2000, U.S. Pat. No. 6,716,578 and is a CIP of U.S. application Ser. No. 09/574,519, filed May 18, 2000, U.S. Pat. No. 6,573,369.

FIELD OF THE INVENTION

The present invention relates to the detection and characterization of pathogens, viruses, and other biological materials.

BACKGROUND OF THE INVENTION

Pathogens constitute a critical problem for human, animal and plant health. Pathogens may cause infections that result in a variety of human illnesses and can lead to a large number of deaths. Such pathogens may include viruses, bacteria, prions, fungi, molds, eukaryotic microbes and parasites of many types. Moreover, pathogens infect agriculturally important plant and animal species, resulting in economic hardship. Detection and identification of pathogens in relevant materials (e.g., water, air, blood, tissues, organs, etc.) is essential to minimize the transfer and spread of infections. Furthermore, quick identification may aid in devising effective treatment strategies.

One class of pathogens is viruses. Viruses are used here as an example and not intended to limit the scope of the invention in any way. Viral infections extol a great morbidity and mortality among the human population. Many of these infections result from undetected viruses in waters, foods and air and are promulgated by an ever-increasing interconnection of societies. Detection and identification in medically-important materials such as blood, blood derivatives, tissues and organs is critical to minimize potentials for transfer and spread within hospitals and clinics and to the staff of these centers.

Several popular methods for the detection and identification of viruses and pathogens exist. These generally fall into three categories: A) Infectivity and infectivity reduction assays; B) Serology assays employing antibody detection to determine whether an individual has been exposed; and C) Direct virology assays in which antibodies are used to detect the presence of an antigen in the sample or nucleic acid-based assays in which elements of the viral genome are detected. Infectivity-based assays are seldom used in diagnostics yet, both cell culture and animal-based amplification of virus in a sample may be necessary for many of the current diagnostic procedures. The use of animals in infectivity assays is costly, time consuming and subject to ethical dispute. Serodiagnosis still exists in many-hospitals principally because there are no good alternatives for some infections. Serology is largely performed to determine antibody levels and to estimate the probability for infection. Antibody based tests are popular, but are usually limited to a battery of individual tests in a macroscopic format (e.g., Enzyme Linked ImmunoSorbant Assay, or ELISA). Standard microbiological approaches to detect anthrax and other bacterial pathogens involve growth of the agent on nutrient agar and visual identification after various staining procedures. Carbon source utilization testing in various media identifies and differentiates among closely related isolates. Viral pathogens are usually identified after their administration, infection and amplification in animals, particularly embryonated eggs, mice or cell culture. This is the basic microbial identification scheme practiced today. While precise in their verification of pathogen identity, these procedures are very slow.

False-positives and false-negatives, particularly in cases where there is known cross reaction with antigens produced by other infections, are of major importance. Polymerase chain reaction (PCR) tests are extremely sensitive and are usually employed in cases where there is prior reason to suspect the presence of a particular pathogen, such as following a positive test for HIV antigens. PCR methods, however, are relatively costly and time consuming. Furthermore, PCR tests are of a relatively limited applicability because of the requirement of enzyme activity and because of the frequency of false positives.

BRIEF SUMMARY OF THE INVENTION

The invention described herein is an affinity capture substrate, or sensor, that can be read by an atomic force microscope (AFM) or another type of scanning probe microscope (SPM) for a simple, rapid, sensitive and high throughput method for detection of pathogens, biological materials, viruses, etc. This method can be applied to detect the target material in a target sample, including whole viruses, viral proteins and viral nucleic acids as well as to distinguish between strains of similar pathogens and biomaterials. Additionally, fluorescence or other methods commonly practiced for detection of biological binding events can be employed when desired.

A method of detecting a target pathogen, comprising the steps of providing a substrate with a surface, depositing a patterned gold layer on the surface, depositing a deposition material on the surface, the deposition material capable of interacting with the target pathogen, and exposing the deposition material to a target sample which can contain the target pathogen and detecting resultant molecular interaction events between the deposition material and the target pathogen by imaging the surface with an atomic force microscope.

An apparatus for the detection of a vaccinia virus, comprising a gold layer deposited on a substrate, an C(x) alkane linker covalently attached to the gold layer, protein A/G tethered to the surface through the alkane linker, and anti-vaccinia antibody deposited on the surface in a domain such that a portion of the deposited antibody retains activity.

A method of detecting a target pathogen, comprising the steps of providing a substrate with a surface, depositing a deposition material on the surface, the deposition material capable of interacting with the target pathogen, exposing the deposition material to a target sample which can contain the target pathogen and detecting resultant molecular interaction events between the deposition material and a target pathogen.

BRIEF DESCRIPTION OF THE DRAWINGS

FIG. 4b is another graphical representation of the chip of FIG. 4a.

FIG. 4c is a representation of an AFM scan of the chip of FIG. 4a.

FIG. 7a is an AFM scan of a chip of the present invention after deposition of a deposition material.

FIG. 7b is a scan of the chip of FIG. 7a after exposing the chip to a target material.

FIG. 7c is a scan of a chip of the present invention after exposing the chip to a control.

DETAILED DESCRIPTION

Definitions

Figure 1:
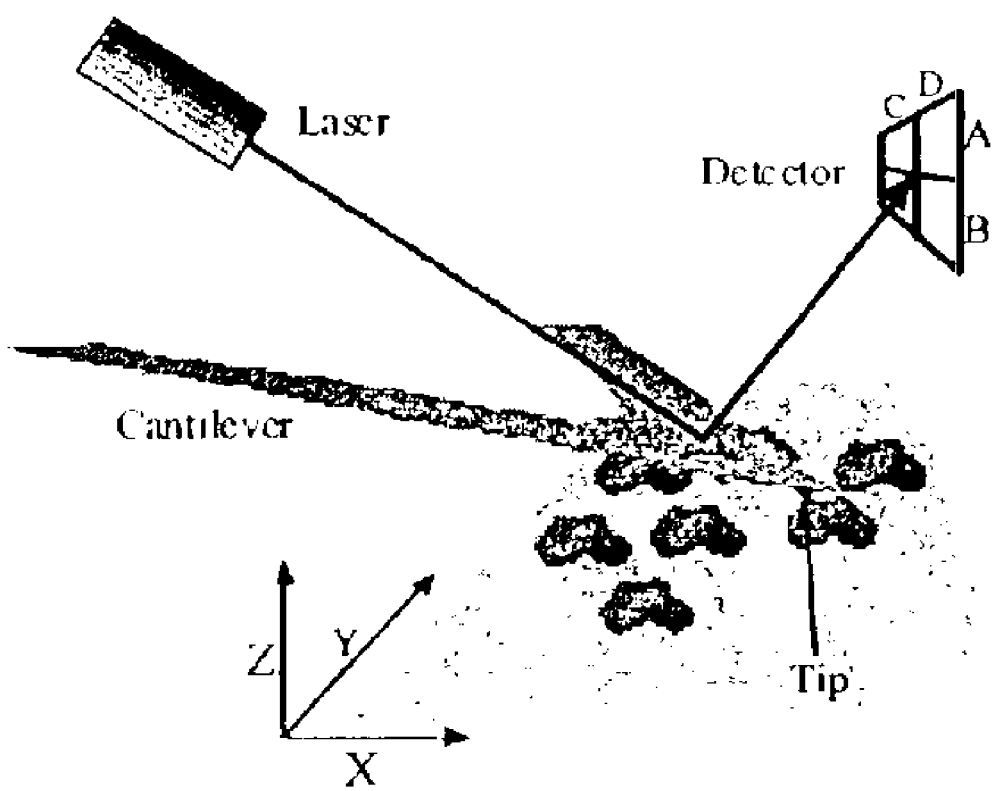
FIG. 1 is an illustration of the AFM detection method.
Figure 2A:
FIG. 2a is a graphical representation of a chip with a deposition material thereon and an AFM scan of the same.
Figure 2B:
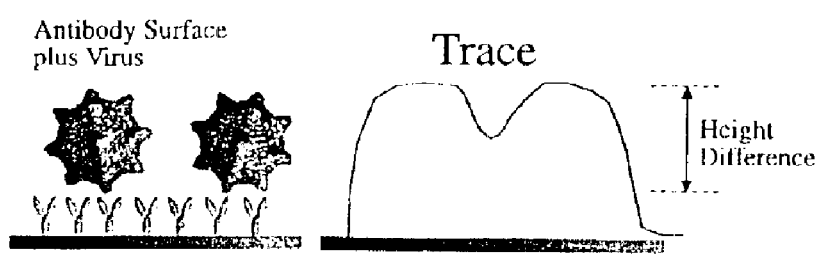
FIG. 2b is a graphical representation of a chip with a deposition material on the surface that has a target material attached and an AFM scan of the same.
Figure 3:
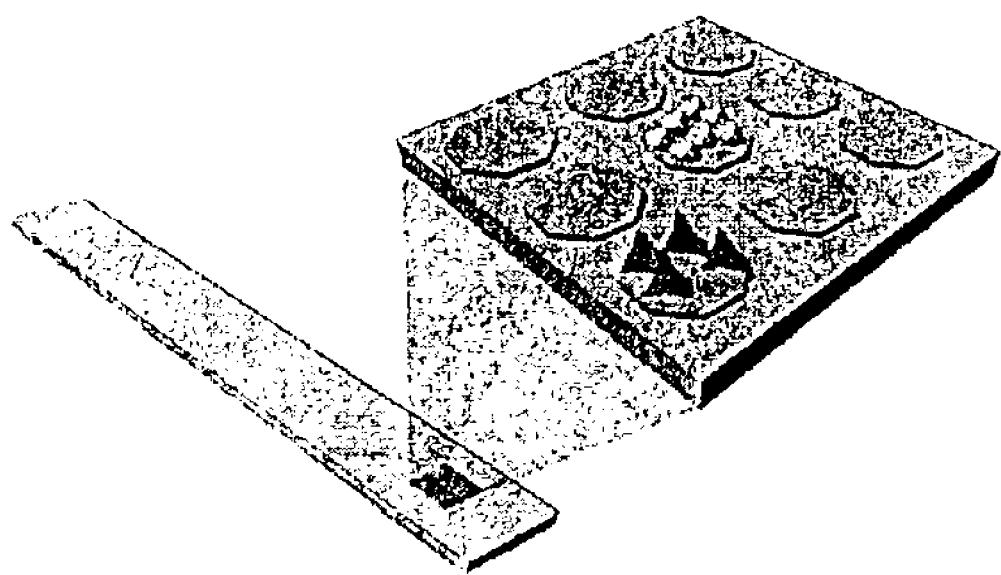
FIG. 3 is a graphical representation of a chip with two different deposition materials placed onto two different deposition domains.
Figure 4A:
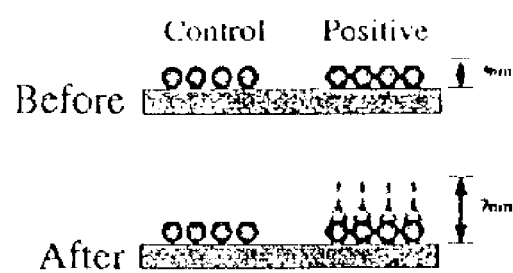
FIG. 4a is a graphical representation of a chip with a deposition material on the surface and a control surface before and after attachment of a target material.
Figure 4B:
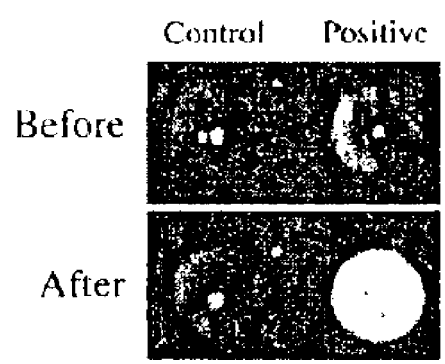
Figure 4C:
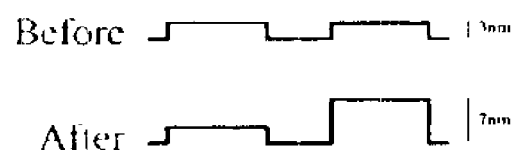
Figure 5A:
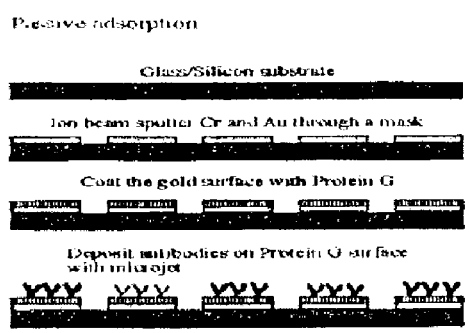
FIG. 5a illustrates the representative layers of a chip where a deposition material is attached by passive adsorption.
Figure 5B:
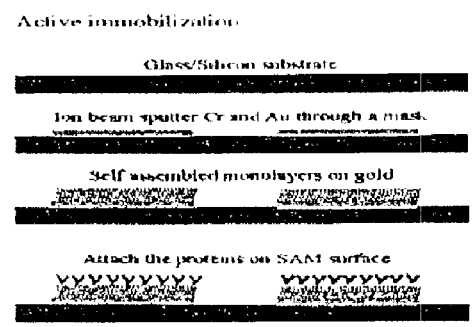
FIG. 5b illustrates the representative layers of a chip where a deposition material is attached by active immobilization.

The following are some definitions that may be helpful in understanding the description of the present invention. These are intended as general definitions and are put forth for a better understanding of the below description but should in no way limit the scope of the present invention.

As used herein the term "pathogen" is used to mean any sort of viral, bacterial, fungal, prion, microbial or other material that can be detected using the teachings of the present invention. The term "pathogen" as used herein can be natural biological agents or artificial materials. Pathogens may include, for example, but not limited to, viruses, eukaryotic microbes, bacteria, fungi, parasites and prions. In particular, pathogens can be a canine parvovirus of the parvoviridae family or a vaccinia virus of the poxviridae family.

The term "target material" is the pathogen that is to be detected.

The term "target sample" is a substance that is being tested to determine whether the target material is contained therein. These target samples can be natural or man-made substances. Alternatively the target sample may be a biologically produced product or an artificially made product. The target samples may be a solution, gas, or other medium.

The term "deposition material" or "deposited material" is the material deposited on the chip for which the target material has some known affinity, such as a binding agent. The deposition material can be deposited in a deposition domain, otherwise known as an affinity domain. The deposition material and the target material can undergo a non-specific binding event, such as, but not limited to, non-specific electrostatic or hydrophobic interactions, or a specific molecular interaction event, such as covalent or ionic attachment. Such deposition materials can include, but are not limited to antibodies, proteins, peptides, nucleic acids, peptide aptamers, or nucleic acid aptamers. In the below described embodiments, the deposited materials are antibodies to known viral pathogens. Antibodies are proteins that bind specifically to a target.

The term "chip" as used in the present invention includes a substrate that has a surface. The "chip" may or may not include the deposition material deposited thereon. Afterwards, the chip is exposed to the target sample to detect the target material.

The present example illustrates the detection of viruses as the target material. The deposition material is the corresponding antibody. The antibody is a naturally occurring or synthetic protein that binds specifically to the target. In the present examples, Canine parvovirus (CPV) and vaccinia virus were detected.

CPV belongs to the Parvoviridae family of viruses and is among the smallest viruses known. Parvoviruses are among simplest eukaryotic viruses and were only discovered in the 1960's. Parvoviral particles are icosahedral, 18–26 nm in diameter and consist of protein (50%) and DNA (50%). The virions are not enveloped and the nucleocapsid confers considerable stability to the particles. There are three capsid proteins, VP1, VP2 and VP3. Infectious virions of CPV contain 60 protein subunits, predominantly VP2.

Vaccinia virus belongs to the poxvirus family and is among the largest viruses known. The vaccinia virus is an analog of smallpox, a designated biowarfare material. Furthermore, the vaccinia viruses are the largest of the DNA viruses affecting humans. The vaccinia virus is enveloped; slightly pleomorphic; ovoid, or brick-shaped. The viral particles are 140–260 nm in diameter and around 220–450 m long. The viral particle is composed of an external coat containing lipid and tubular or globular protein structures enclosing one or two lateral bodies and a core, which contains the genome. Nucleocapsids are brick-shaped to ovoid. The core is usually biconcave with two lateral bodies.

To form a chip that comports with the teachings of the present invention, a substrate must first be prepared. Substrates were prepared using #1 glass cover slips (Fisher Scientific) that were cut into 7 mm×7 mm squares and cleaned thoroughly for 30 min in ethanol using an ultrasonic bath. The glass substrates can be stored in ethanol until ready for use. The glass substrates were then coated with a thin layer (~3 nm) of chromium at 0.1 nm/s followed by the deposition of 20 nm gold at 0.2 nm/sec using an IBC 2000 (South Bay Technologies). The surface was patterned by placing a copper electron microscopy grid (400 mesh, hole size 100 um, bar size 15 um) (Electron Microscopy Sciences) on the glass during the coating process forming 100 um$^2$ gold pads on the glass surface. A slot grid (200×600 um) or a single hole grid (600 nm) can alternatively be used to pattern the surface. In preliminary studies, it has been observed that antibodies bind tenaciously to bare (clean) gold surfaces and retain some level of biological activity. The virus particles can also bind to gold and create a background problem.

Passive adsorption was utilized to attach protein G to the gold surface to keep the non-specific binding of the virus particles to a minimum. Protein G is utilized as a layer over the surface because protein G presents four binding sites and orients the antibodies. Protein G is a naturally occurring protein that binds tightly to the Fc region of antibodies, in particular, IgG. In addition, when an antibody is deposited on the protein G, each antibody will orient in a specific manner relative to the surface. Control of the manner in which the antibodies orient relative to the surface insures that more of the active antibody binding site is exposed and active. In one alternative embodiment for passive adsorption, another protein can be used, for example, protein A (similar to protein G) or a hybrid protein A/G, (a recombinant mixture of protein A and protein G that combines the binding characteristics of both). In other embodiments, the chip may utilize the deposited gold surface to bind the antibody to the surface in a non-specific way. In still further embodiments, the gold surface can be covered with an alkanethiolate material so that the deposited antibody coupled to the surface in a very specific manner, e.g., chemically (see Example II below).

To deposit the protein G layer, the glass substrates with the freshly prepared gold pads are immersed in a protein G (Sigma) solution at 1 mg/ml in 1xPBS (10 mM phosphate buffer, 137 mM NaCl and 1.37 mM KCl) at room temperature for 30 minutes. Protein G is passively absorbed onto the prepared gold surface forming a uniform protein surface over the gold coated glass substrates. The substrate was then removed from the protein solution, washed with filtered distilled water, blown dry with argon, and stored at 4° C. until antibody deposition.

Antibodies can be deposited on the surface using a microjet device similar to the inkjet used in a inkjet printer. The microjet apparatus and method uses an aerosol microdroplet to create domains of the antibody on the surface. In the present embodiment, a single microjet, with a 30 um nozzle, and a MicroJet III controller (MicroFab Technologies, Inc., Texas) was used. The microjet was mounted on custom-built computer controlled stage with translation along the X, Y and Z axes. Deposition domains of anti-viral antibodies on the order of few tens of microns were created in the protein G surface.

The microjet method offers the advantage of extensive field testing and previous utilization in commercial applications involving genome arrays. The microjet uses a piezoelectric pump for precise delivery of fluids in the nanoliter to picoliter range. The microjet can consistently make arrays of antibodies with spot sizes in the 30–80 um diameter range separated by 20 um. Using spot sizes of 50 um and inter spot distance of 20 um, production of a 2x2 array in a 120x120 um area can be achieved. The AFM scan range is approximately 120 um and therefore can interrogate all four spots in a single AFM scan field.

Subsequent to antibody deposition, the substrates were re-hydrated by placing them in a high humidity environment for 30 minutes, such an environment may be greater than 50% more preferably about 90%. Exposing the chip to high humidity and re-hydrating the chip helps the antibody to bind to the protein G surface.

Typical viral diameters may range from about 20–200 nm. It is not crucial for every antibody to retain biological activity, therefore, because the viral particles are significantly larger than a single antibody and will cover a field of several antibodies. A virus with a radius of 25 nm (roughly the size of the CPV) would cover an area of about 500 $nm^2$ when touching a surface with sufficient molecular flexibility to permit antibodies to gain access to 25% of the viral surface. The antigen binding site of an antibody covers a spatial envelope of approximately 2 nmx5 nm, or 10 $nm^2$. Therefore, if only 20% of the antibodies on the surface were correctly oriented and biologically active, the viral particle would contact about 10 potential binding sites. Based on these considerations the present embodiment uses chemisorbed antibodies for the construction of the solid state viral detection and identification assay.

The chip is then exposed to the target sample and tested for any molecular interaction events between the deposited material and the target material.

As illustrated in FIG. 1, the present invention utilizes an atomic force microscope as the detection apparatus. In an AFM, the interactions between a sharp, micron-scale probe and a sample are monitored and regulated as the probe scans over the sample. Extremely fine control of the motion of the AFM probe is achieved using piezoelectric crystals. Thus, the AFM is capable of ~2 nm lateral resolution and <1 nm vertical resolution. This level of resolution gives the AFM the ability to detect changes in topography in the Angstrom range. The ability of AFM to detect height changes on the order of 1 nm has been utilized for the detection of antibody-antigen interaction; AFM has also been used to image nucleic acids, proteins, viruses, bacteria, live cells and other biological materials. The AFM can be operated in solution and is capable of identifying molecular binding events in near-real time. For a typical AFM immunoassay, the change in height is on the order of 1–3 nanometers (nm), providing a change in signal of 100% (from 3 to 6 nanometers, for example). For viruses, this change is much greater, on the order of 30 to 300 nm, providing a signal to noise ratio of 10 to 100 fold.

A Dimension 3000 series AFM (Digital Instruments/Veeco, Santa Barbara, Calif.) equipped with a 120-um tube scanner was utilized for the large-scale topography measurements of the chip. All images were captured in Tapping mode using silicon ultralevers (Park Instruments) under ambient conditions. Images were flattened and low pass filtered for analysis.

Although the present embodiment utilizes the AFM as a label-free detection device, alternative methods including, but not limited to, surface plasmon resonance, mass spectrometry, electronic signature, optical methods, or other techniques, can be incorporated into the present invention without changing the nature and scope thereof.

EXAMPLE I

With reference to FIGS. 2a–b, 4a–c, 5a, 6a–c, and 7a–c, CPV is detected by constructing a chip with anti-canine parvovirus monoclonal antibody deposited thereon, exposing the chip to a target sample, and then reading the chip using the AFM to determine whether CPV is bound to the chip surface.

The viral particles were prepared at a stock concentration of 0.3 mg/ml. Purified monoclonal antibody which recognizes the CPV capsid, A3B10 (0.9 mg/ml) was utilized. In another test run, purified anti-canine parvovirus monoclonal antibody (2 mg/ml) was obtained from a separate source (Custom Monoclonal International, California) with no observable change in results.

A chip with a protein G coated surface was used for the deposition of antibodies against CPV at specific regions. The domains were formed using the above described microjet method. The antibodies of the present embodiment were diluted to 0.1 mg/ml in 1xPBS before being deposited onto the surface using the microjet. The microjet was back-loaded with a syringe and the anti-viral antibodies were deposited on the surface with spot sizes in the range of 40 to 80 um. After all the antibodies spots were deposited, the chips were incubated in a humid environment for 30 minutes at room temperature to allow the antibodies to bind to the protein G surface. The chips were then washed with distilled water, blown dry with Argon and stored at 4° C. until used.

Figures 6A, 6B, 6C:
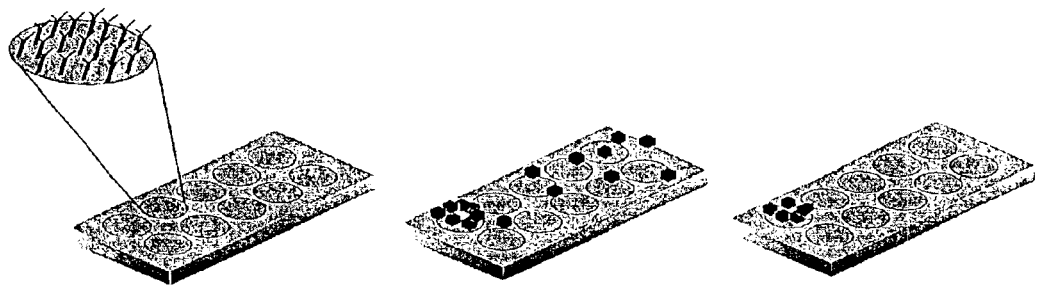
FIG. 6a is a perspective view of a chip of the present invention with deposition material deposited thereon.
FIG. 6b is a perspective view of a chip of the present invention after being exposed to a target sample containing a target material.
FIG. 6c is a perspective view of the chip of FIG. 6b after washing.
Figures 7A, 7B, 7C:
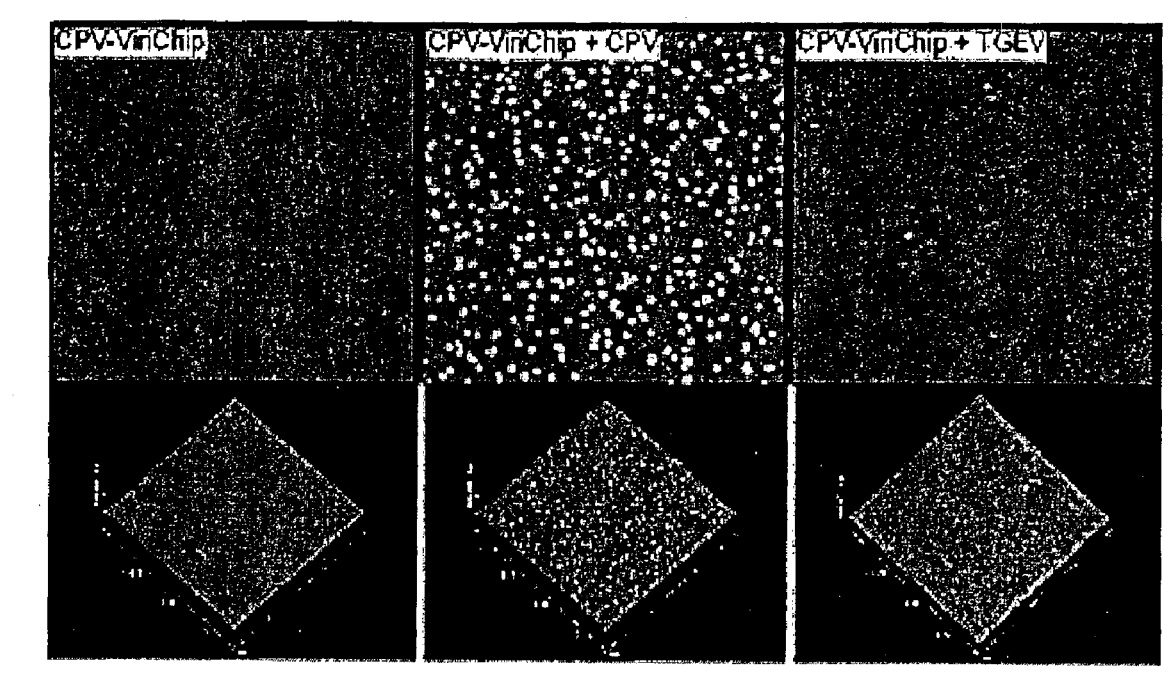
Figure 8:
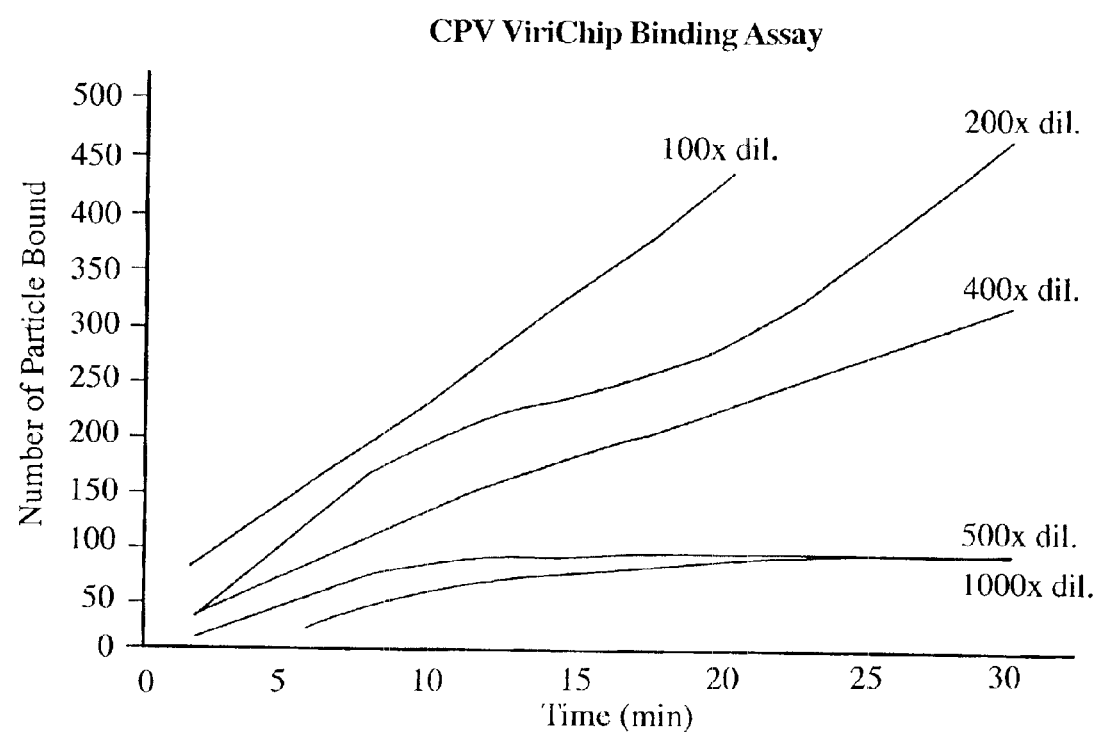
FIG. 8 is a graph of the number of target material particles bound to a chip surface versus exposure time for various concentrations of target material.

After the desired surface was formed on the chip, the chip was washed with distilled water and imaged to insure the surface was clean and smooth with no particulate matter thereon. Such an image is seen in FIGS. 7a and 6a. The present embodiment utilized incubation of the antibody with the chip to expose the deposition material to the target material. The chips were incubated with the target sample, in this case 200 µl of virus detection buffer (PBS containing 0.25 mM NaCl, and 0.2% tween-80) on a rocker platform at room temperature for 15 min. During the incubation with CPV, the virus binds not only to the specific domain on the chip with CPV antibodies but also binds non-specifically to other regions on the chip. See FIG. 6b. Following incubation, the chips were washed three times in wash buffer (PBS containing 0.4 M NaCl and 0.2% T-80), each for 10 min. and once in water. This removes the non-specifically bound virus (FIG. 6c). Each chip was rinsed in water and blown dry in a stream of argon and then imaged by AFM. The chips may be incubated in 2 µl at high CPV concentrations (>100 ng/ml). At lower viral concentrations, the chips can be incubated in 200 µl of viruses in the target sample detection buffer for varying lengths of times on a rocker at room temperature.

Results

The above steps were used to test samples containing CPV at various concentrations. Afterwards, each chip was imaged and a particle count analysis was performed. Five sets of data were collected and plotted on a graph with the time on the X-axis and number of virus particles bound on the Y-axis. As seen in FIG. 8, as the concentration decreases the number of virus particles bound at any given time also decreases. Also, at any concentration the binding profile seems to follow a standard asymptotic curve as would be seen for a single step binding profile.

The regions where the CPV antibodies were deposited had virus particles bound to it (>500 particles/5 um region). Areas where no antibodies were bound had very few virus particles bound to it (<10 particles/5 um region). The bindings where no CPV antibody was deposited can be attributed to non-specific interactions between the virus with the protein G surface. See FIGS. 7*a–c*.

By performing a dilution series experiment with CPV, it was determined that virus particles can be detected at a concentration of 300 pg/ml. The CPV genome is about 5 kilobases of single stranded DNA. Assuming the molecular weight of the total DNA is equal to that of the proteins, the molecular weight of the empty capsids would be about 2000 kDa., then 1 $\mu$g of the empty capsids would have about $3\times10^{11}$ particles (stock concentration of $10^{14}$ particles/ml). These numbers indicate that viruses at a titer of $10^7$ particles/ml will provide a signal that is sufficient to report the presence of a particular virus.

More quantitative data analysis can be performed to relate the degree of observed binding to the sample concentration. For example, since the number of particles observed is a function of time, which is derivative of the sample concentration, it is possible to carry out a time course and determine an absolute sample concentration. The number of viruses bound at several time points, for example, 1, 5, 20 and 60 minutes, is measured. This can be compared to a standard curve for virus at known concentrations. Since the binding is driven by diffusion and therefore the number of binding events per unit time is a function of concentration, one can calculate the concentration of the unknown virus by fitting the binding vs. time curve to the standard curve obtained using the known concentrations of virus.

This data can be coupled with morphological analyses, local adhesion, elasticity, viscosity, or other analyses of which the AFM is capable, to create a multidimensional database of information which greatly enhances the identification and characterization of materials bound to the sensor surface.

FIGS. 7*a–c* represent AFM scans of a chip surface. The upper image shows a two dimensional rendering in which scale indicates topographical features. Lighter intensity features are taller than darker features (total Z range 300 nm) and the field size is 2 $\mu\times2$ $\mu$. The lower image is a 3D projection of the same data. FIG. 7*b* shows the surface after reaction with CPV. The lighter features correspond to the presence of bound CPV particles.

An example image of the virus binding to the microarray using AFM is illustrated in FIGS. 2*a–b*. Thus, when no sample is present, the deflection of the probe is due to the presence of the capture probe (Control). When sample is bound to the capture probe, the increased height of the deflection is due to the bound, large molecular weight particle sitting on top of the capture probe and is clearly detected (Positive). This analysis allows for quantification of particles bound to the chip by integrating the number of capture probes per spot bound to target particles.

As illustrated in FIGS. 6*a–c*, each antibody specific for a unique virus can be spotted on a distinct domain. When the entire chip surface is exposed to the virus, viral particles will bind strongly to the domain with its specific antibodies but will also non-specifically bind weakly to other domains. See FIG. 6*b*. After washing the chip surface, most of the weak, non-specific binding of the antigen is removed and remaining surface binding of the antigen is specific to the domain with its antibody. See FIG. 6*c*.

In the present invention, the results of binding can be checked by utilizing a control. A control is effectuated by exposing the virus to a chip, which does not have a binding affinity to the target material. In the present embodiment, the chip for detecting TGEV was exposed to CPV. FIG. 7*a* shows the chip surface as detected by AFM with no analyte added (control). FIG. 7*c* shows a chip against Transmissible Gastroenteritis Virus (TGEV), reacted with CPV, which should not bind to the anti-TGEV antibody on the chip (non-specific binding). In this case, very little non-specific binding occurs, as reflected by the absence of raised features (viral particles). Such a rendering was also performed with antibodies against CDV (Canine Distemper Virus) with similar results. (Purified Monoclonal Anti distemper virus antibody (0.1 mg/ml) was obtained (Biodesign International, Maine)).

EXAMPLE II

Anti-vaccinia and anti-adenovirus (control) antibodies were obtained from Biodesign. Vaccinia virus strain WR (American Type Culture Collection (ATCC) 1354) was grown in HeLa S3 (ATCC CCL-2.2) cells maintained on RPMI 1640 supplemented with 7% v/v fetal bovine serum and penicillin, streptomycin and fungizone. Near confluent S3 cells in Blake bottles were infected at a multiplicity of infection (MOI) of 0.2. Cells were collected when detachment became apparent in about 3 days. Virus was purified from frozen and thawed cells by successive cycles of sedimentation velocity and equilibrium density centrifugation. Stocks of purified virus were titered by end-point dilution assays and stored at −80C. The virus had a stock concentration of $10^7$ pfu/ml. The purified rabbit anti-vaccinia (B65101R lot 8304600) and goat anti adenovirus hexon (B65101G, lot 4A01901) antibodies were divided into aliquots and stored at −20 C. until use.

To construct the vaccinia chips, the process of active immobilization to adhere anti-vaccinia antibodies to the chip surface was utilized instead of the passive adsorption to a protein layer as described in Example I above. In contrast, few adenovirus particles bind to the vaccinia chip demonstrating the specificity of vaccinia chip. Further characterization of the vaccinia chip showed that the binding of vaccinia to the chip was linear with time for the first 12 hours with a maximum of 200 particles attached in a 900 $\mu^2$ area viewed by AFM.

The anti-vaccinia binding agent can be tethered to the surface by first placing an alkanethiolate monolayer over the gold. The anti-vaccinia virus would then be reacted with a —COOH group on the exposed portion of the alkanethiolate. In other embodiments, the binding agent can be tethered with a succinimide group or a $NH_2$ group.

The virus retains its typical brick-like morphology. The virus may retain some or all of its infectivity as the placement of the washed and dried chip onto a HeLa S3 monolayer resulted in infection from which infectious vaccinia virus was obtained.

The anti-adenovirus antibody in the heterologous experiment did exhibit a few bound virions. The ratio of homologous to heterologous signal in several experiments using these antibodies is about one log. Typically 3–8 vaccinia particles were detected in a 900 $\mu^2$ field using anti-adenovirus.

For actively immobilized antibody attachment to chip surfaces, freshly prepared gold surfaces, which were patterned through a slot grid or a single-hole grid, were immersed overnight at room temperature in a 0.5 mm ethanolic solution of 16-mercaptohexadecanoic acid. The surfaces were rinsed in ethanol and activated by incubating in 1-Ethyl-3-(3-Dimethylaminopropyl)carbodiimide (EDC) (10 mg/ml in 100 mM (2-(N-Morpholino)ethanesulfonic acid) (MES) buffer pH 4.8) at room temperature for 2 hours. Each chip was rinsed in PBS and blown dry in a stream of dry argon. The central gold pattern (formed by the slot grid) were covered with 1 $\mu l$ of the antibodies (0.1 mg/ml in PBS) and incubated at room temperature for 2 hours. The chips were then rinsed in PBS and the un-reacted chip surface was blocked by incubating in 10 mM methylamine in PBS for 30 minutes. The chips were washed with water, blown dry and stored at 4° C.

From an assay that contained $10^5$ infectious doses per ml and an estimated particle number of $10^6$ based upon TEM the assay was linear with time for the first 12 hours with a maximum of 200 particles attached in a 900 $\mu^2$ viewed by AFM.

Binding was a function of concentration. Increasing the concentration by 30 fold resulted in a 30-fold increment in virus numbers observed.

Alternative Embodiments

In one alternative embodiment, larger spots can be used in conjunction with a mechanism for rapid translation of the sample under the scanning probe. In this embodiment, spot sizes of 60–100 $\mu$ diameter can be positioned a few tens of microns apart in the array. The AFM would then scan the spots in a known order, relying on accurate translation of the spots to the interrogation field. This operation may be readily accomplished using a conventional high resolution translation stage. Throughput would not be compromised because faster scan rates (e.g., 3 Hz vs. 1 Hz) and lower resolution (e.g. 256 vs. 512 lines per scan) data could be employed to offset the additional time required to physically translate the stage without introducing intolerable degradation of data.

As may be appreciated, the invention can be applied to detection and characterization of a broad range of biological materials, such as, but not limited to, other viruses, bacteria, bacterial spores, prions, pathogenic microbes such as fungus, parasites, mold, and pollen spores.

The information and examples described herein are for illustrative purposes and are not meant to exclude any derivations or alternative methods that are within the conceptual context of the invention. It is contemplated that various deviations can be made to this embodiment without deviating from the scope of the present invention. Accordingly, it is intended that the scope of the present invention be dictated by the appended claims rather than by the foregoing description of this embodiment.

We claim:

1. A method of detecting a target pathogen, comprising the steps of:
providing a substrate with a surface;
depositing a patterned gold layer on the surface;
depositing a deposition material on the surface, the deposition material capable of interacting with the target pathogen; and
exposing the deposition material to a target sample which can contain the target pathogen and detecting resultant molecular interaction events between the deposition material and the target pathogen by imaging the surface with an atomic force microscope.

2. The method of claim 1 wherein the pathogen is a virus and the deposition material is an antibody.

3. The method of claim 1 wherein the surface is chosen from the group consisting of glass and silicon.

4. The method of claim 1 wherein the patterned gold layer is sputtered on the surface.

5. The method of claim 1 wherein the surface further comprises a layer of chromium.

6. The method of claim 2 wherein the antibody is attached to the surface by spontaneous adsorption.

7. The method in claim 2 wherein the antibody is chemically tethered to the surface.

8. The method of claim 2 further comprising depositing an orienting protein layer on the surface to orient the antibody.

9. The method in claim 8 wherein the orienting protein is chosen from a group consisting of Protein A, Protein G and Protein A/G.

10. The method of claim 8 wherein the orienting protein is passively adsorbed on the gold surface.

11. The method in claim 8 wherein orienting protein is chemically tethered to the surface.

12. The method of claim 8 further comprising covalently attaching a C11–C18 alkane linker to the gold layer.

13. The method in claim 12 wherein the alkane linker includes a functional portion selected from a group consisting of a COOH, a $NH_2$, and a succinimide.

14. The method of claim 12 wherein the alkane linker interacts with a primary amine of the protein.

15. The method of claim 2 wherein the antibody is deposited using an inkjet.

16. The method of claim 15 wherein the antibody is deposited in a deposition domain on the surface.

17. The method of claim 8 wherein depositing the antibody to the orienting protein further comprises incubating the surface with the antibody thereon in a humid environment to allow the antibodies to passively bind to the orienting protein.

18. The method in claim 17 wherein the excess antibodies are washed from the surface following the binding event.

19. The method of claim 2 wherein the virus is canine parvovirus.

20. The method of claim 19 wherein the antibody is anti parvovirus.

21. The method of claim 2 further comprises exposing the virus to a control antibody.

22. The method of claim 21 wherein the control antibody is anti-transmissible gastroenteritis virus.

23. The method of claim 21 wherein the control is anti-canine distemper virus.

24. The method of claim 2 wherein the virus is a vaccinia virus.

25. The method of claim 24 wherein the antibody is a monoclonal antibody directed against a vaccinia virus.

26. An apparatus for the detection of a vaccinia virus, comprising
   a gold layer deposited on a substrate;
   an C(x) alkane linker covalently attached to the gold layer;
   a protein A/G tethered to the surface through the alkane linker; and
   anti-vaccinia antibody deposited on the surface in a domain such that a portion of the deposited antibody retains activity.

27. The apparatus of claim 26 wherein the substrate, the gold layer, alkane linker layer, protein A/G and the antibody deposited thereon form a chip.

28. The apparatus of claim 26 wherein x is a carbon backbone of 11 to 18 carbons in length terminating with a succinimide group.

29. The apparatus of claim 26 wherein the apparatus further comprises a control antibody deposited on the surface in a domain.

30. The apparatus of claim 29 wherein the control is anti-adenovirus antibody.

31. The apparatus of claim 26 wherein the antibody is microjet deposited.

32. The apparatus of claim 26 wherein the substrate is selected from the group consisting of glass and silicon.

33. The apparatus of claim 26 wherein the gold layer is deposited on the surface in a grid pattern.

34. The apparatus of claim 33 wherein the grid pattern is a 400 mesh grid with a hole size of 100 um and a bar size of 15 um.

35. The apparatus of claim 33 wherein the grid pattern is a slot grid of 200 um by 600 um.

36. The apparatus of claim 33 wherein the grid pattern is a hole grid pattern of 600 um.

37. A method of detecting a target pathogen, comprising the steps of:
   providing a substrate with a surface;
   depositing a deposition material on the surface, the deposition material capable of interacting with the target pathogen;
   exposing the deposition material to a target sample which can contain the target pathogen and detecting resultant molecular interaction events between the deposition material and a target pathogen.

38. The method of claim 37 further comprising depositing a second deposition material on the surface capable of interacting with a second target pathogen before exposing the deposition material to a target sample which can container one or more of the target pathogens.

39. The method of claim 37 wherein the deposition material is a virus and the target pathogen is a virus.

40. The method of claim 37 wherein the deposition material is an aptamer.

* * * * *